United States Patent [19]

Keiner

[11] Patent Number: 5,254,329
[45] Date of Patent: Oct. 19, 1993

[54] METHOD FOR IMPROVING VISUALIZATION OF SEROTONERGIC STRUCTURES IN NONHUMAN VERTEBRATES

[76] Inventor: Melvyn H. Keiner, 436 Main St., Spotswood, N.J. 08884

[21] Appl. No.: 667,522

[22] Filed: Mar. 11, 1991

[51] Int. Cl.$^5$ ............. A61K 49/00; A61K 49/02
[52] U.S. Cl. ............................ 424/9; 424/3; 424/4; 435/7.21; 435/7.9
[58] Field of Search ........................ 424/4, 9

[56] References Cited

PUBLICATIONS

Wallace et al–Chem. Abst. vol. 97 (1982) p. 208, 653a.
Mathura et al–Chem. Abst. vol. 105 (1986) p. 219 421h.

*Primary Examiner*—Sam Rosen

[57] ABSTRACT

A method for the visualization of serotonergic cells in the dorsal raphe of living nonhuman vertebrates by pretreatment with L-tryptophan significantly less than one hour prior to sacrifice reveals numerous structures and cell types hitherto unidentified when combined with immunocytochemistry, immunofluorescence, or serotonin tagged autoradiography in the light microscope.

21 Claims, No Drawings

METHOD FOR IMPROVING VISUALIZATION OF SEROTONERGIC STRUCTURES IN NONHUMAN VERTEBRATES

BACKGROUND AND SUMMARY OF THE INVENTION

1. Field of the Invention

This invention relates to a method for the enhancement of serotonergic structures for the purpose of improving their visualization under microscopic examination by various techniques. This invention is particularly suitable for, but not limited, to the serotonergic raphe of the brainstem of nonhuman mammals.

2. Description of Prior Developments

For the understanding and, hence, rational treatment of neurologic and psychiatric diseases of serotonergic dysfunction it is desirable to be able to visualize in as much detail as possible the various manifestations of the structural elements in the serotonergic raphe of the hindbrain and the midbrain.

In vertebrates the midbrain is primarily responsible for the production and distribution of the neurotransmitter serotonin (5-hydroxytryptamine, 5-HT) that is distributed to numerous forebrain structures involved in diverse behavioral and physiological functions. The dorsal raphe is the site of the majority of serotonergic cells thus far counted by immunocytochemical (alternately called immunohistochemical) techniques, and, hence, the primary source of serotonin in the central nervous system.

With traditional methodology, which has been used extensively, the serotonergic raphe is essentially similar within all, or most, species of vertebrates at numerous taxonomic levels. The raphe is phylogenetically old and conservative throughout phylogeny, testifing to its fundamental importance in vertebrates, including man.

To enhance the visualization of serotonergic cells in living nonhuman vertebrates, a common procedure is to pretreat the organism with L-tryptophan, the dietary amino acid precursor of the neurotransmitter serotonin. L-tryptophan is converted in two enzymatic steps to serotonin and the pretreatment is considered a method to increase the amount of neurotransmitter in the brain. It has been postulated that this is not a physiological treatment but a pharmacological one and is artifactual. Not all investigators pretreat with L-tryptophan.

All previous studies use a pretreatment time of from one to four or more hours prior to sacrificing the experimental animals. The rationale accepted in the prior art is that it takes considerable time for serotonin to be synthesized in the animal.

In conjunction with L-tryptophan pretreatment, a drug that blocks serotonin uptake at the synapse, hence preventing its catabolism, may be added to enhance the amount of neurotransmitter available for visualization.

The central importance of the dorsal raphe in the brainstem raphe in general is indicated by the quantity of neurotransmitter manufactured, number of serotonergic cells, and the amount and distribution of its efferent and afferent fibers.

SUMMARY OF THE INVENTION

Accordingly, an object of the present invention is to provide an improved method of L-tryptophan pretreatment in order to enable adequate visualization of serotonergic tissue structure in the microscope.

As herein described, there is provided a method for examining a serotonergic tissue structure of a nonhuman vertebrate by preparing the said vertebrate while alive, under controlled conditions, intravenously injected with L-tryptophan, within one hour prior to sacrifice, for preparation and observation by different microscope techniques.

GENERAL DESCRIPTION

The invention is a method of administering intravenously, L-tryptophan, for a time preceding sacrifice considerably less than the prior art, notably less than one hour, in order to visualize by traditional histological techniques appropriate to reveal serotonergic structures of the raphe system of the hindbrain and the midbrain, especially mammals.

This invention has thus far demonstrated many unique cell structures and cytoarchitectonic characteristics of the dorsal raphe and immediately dorsal subependyma and ependymal tissue ventral to the aqueduct of Sylvius that are not known to the prior art. The prior art for visualization of serotonin immunocytochemically utilizes pretreatment of one to four or more hours prior to sacrifice, or no pretreatment with L-tryptophan at all. It is believed that the increase in serotonin caused by the two enzymatic steps converting L-tryptophan to serotonin in the raphe requires significantly more time than proposed here.

The most common histological preparation is immunocytochemical but may also be immunofluorescence, autoradiography or a combination of immunocytochemical or immunofluorescence in combination with autoradiography by using a radioistope tagged to serotonin injected variously into the ventricular system, in the belief that serotonergic cells sequester, as well as, produce serotonin.

DETAILED DESCRIPTION

The method invention herein described was developed from the prior art using the rat brain.

The rat is a very appropriate experimental animal in biomedical research. It is utilized far more than any other species of mammal (or other vertebrate). It is small, easily housed, inexpensive, and neuroanatomically very similar to the human brain on the light microscope level. There is no reason to indicate observations in the rat to be appreciably different than any other mammal. In fact, from the literature, there is no reason to suspect significantly different results in vertebrates other than mammals.

Numerous serotonergic cell structures, previously unreported, abound in only a small portion of the total raphe system, a neuroanatomical entity extending from the hindbrain to the midbrain, when combined with a change in the method of L-tryptophan pretreatment, namely, within less than one hour of sacrifice of the experimental animal.

The prior art has assumed that the conversion of L-tryptophan, a dietary amino acid, to serotonin, a neurotransmitter, in two enzymatic steps, occurs slowly. Relying on this assumption, the pretreatment of all experimental vertebrates studied with intravenous administration of L-tryptophan have been sacrificed from one to four or more hours after the administration of the serotonergic precursor.

Moreover, other investigators of the prior art have avoided the use of L-tryptophan, believing that it is an unnatural technique and may produce artifactual results. They have considered L-tryptophan to be a pharmacological treatment rather than a physiological one. Nevertheless, the prior art makes extensive use of L-tryptophan pretreatment one hour or more.

The prior art gives a hint of the rapid conversion of L-tryptophan into serotonin: In glia in tissue culture (Bauman); in neurons in tissue culture uptake is considerably faster (Graham-Smith); and, in vivo serotonin production reaches a steady state in 30 minutes.

The biosynthesis of serotonin is a complex process not only involving the precursor L-tryptophan. Generically diverse chemical entities may be involved from the protein, insulin, to carbohydrates such as fructose, to vitamins, and minerals (Pollack).

The change in art reported here was determined by investigating the Dorsal Raphe Nucleus (DRN), sometimes identified as B7, in the midbrain. The subependyma, immediately dorsal and lateral, to the DRN proper, and ventral to the aqueduct of Sylvius, was also investigated.

Cells previously unreported have been identified.

Strikingly, in the DRN proper a structure consisting of bilaminar planes, with alternating neuronal and glial cells, one cell thick oriented 45 degrees to the longitudinal axis in the transverse plane with crossed fibers between the two very different planes in terms of cytoarchitecture and extracellular matrix, has been identified.

Increasing magnifications demonstrate the considerable complexity of this neuroanatomical structure in terms of somata and cell processes, at 1625x, approaching the limiting, meaingful magnification, dependent on the resolving power, of the light microscope. Increasing magnification is inversely proportional to decreasing depth of field, hence, the thickness of the section which is 100 micra, was divided approximately into six adjacent focal planes of about 16 micra each, less than the dimensions of the cells observed.

The neuronal plane (RFP) has been traditionally observed by the prior art. The glial plane (CFP) has never before been observed. The repeating, alternating nature of these two planes can only be visualized by the present invention, namely, pretreatment with L-tryptophan prior to one hour of sacrifice.

The continuity of the glial and neuronal planes can be proven by examination of the four transitional planes.

Structures in the glial plane can be followed in subsequent transitional planes till they disappear; conversely, structures in the neuronal plane can be followed in the opposite direction till they disappear.

The planes do not overlap. The cytomorphology of the two planes is extremely distinct. The extracellular matrix of the two planes is distinct. Density of somata and fibers is considerably greater in the glial plane. Orientation of cells and fibers within the transverse sections are very different for the two structures. In the glial plane the fibers appear to be oriented at random while in the neuronal plane they are distinctly parallel, 54 degrees from a horizontal. At least, a significant portion of fibers in the neuronal plane cross the midline.

The fibers of the neuronal plane are axons that travel in the interface between the glial and neuronal plane, hence, their parallel orientation.

The present invention is supported by authoritative representatives of the prior art who report only small numbers of axonal radiolabelled serotonergic varicosities in spaced consecutive sections in the DRN (Descarries et al). Conceivably, the glial plane was examined, not the neuronal plane, hence, radioisotopic serotonergic uptake by neurons was minimal because glial may only synthesize serotonin, therefore, would not be visualized by the prior art unless the neurotransmitter was synthesizing serotonin from radiolabelled L-tryptophan. The number of somata in the glial plane is about 30% greater than the neuronal plane. The cell aggregations in the neuronal plane are predominantly singular with the extracellular matrix separating somata by about two cell body distances. In the glial plane, somata are found in groups of two to five, each group being closer to the others and separated by less extracellular space. Glial cells lack elongate fibers, instead contain numerous very varied appearing large and small appendages often changing their cross-section diameter. Their shape is irregular often approaching a circular or oval form. Neurons are obvious, often uni- or bipolar and some are multipolar. The fibers, probably axons, are uniform in diameter although they may decrease in a consistant manner with distance from the soma. Most significantly, the glial plane is less stained than the neuronal plane. Visualization of the glial plane, especially for photomicroscopy, made use of the optical technique called modulation contrast to enhance visibility. The prior art did not permit visualization of the glial cells. The invention permits the very rapid uptake of L-tryptophan, perhaps, peaking within minutes (Bauman et al) although it may take as much as a half hour for the steady state to be reached (Hery et al). In order for a structure to be visible in the light microscope, it usually, must take a stain. Assuming that the serotonin rapidly produced is quickly and swiftly and actively transferred to the extracellular matrix of the CFP where diffusion leads to neuronal sequesterization, producing a concentration gradient. As a result, even while manufacturing serotonin, these unique cells (probably type 1 astrocytes) may be light-staining. A representative of the prior art informally concluded definitively that the histological material used for this invention was defective when it was pointed out to him that the DRN proper on gross visual inspection was lighter-staining than the surrounding area. This lightening is the sum of stained and unstained serotonergic structures and the surrounding area obviously took more stain because it lacked the glial synthesizing cells. Had the prior art been used, the serotonergic stain here would have been uniform throughout the section. A bilaminar distribution of neuronal glial cells also exists in the medial subependyma ventral to the aqueduct of Sylvius and has not been reported in the prior art.

The glial subependyma is found caudal to a neuronal subependyma. The medial dorsal extension into the aqueduct of the tuft-like structure is blurred, indicating an out-of-focus figure actually representing the dorsal extension of the neuronal subependyma more rostrally. The glial subependyma does not extend into the aqueduct. This limit appears as a hollow channel, possibly containing aqueductal circumferential fibers.

The intensification of immunoserotonergic stain by this invention more easily displays herring bodies than the traditional treatment. Herring bodies are frequent in the subependyma and are considered accumulations of secretory products. The herring body here is in sharp focus in the glial plane, supporting the contention of rapid conversion of L-tryptophan into serotonin in the glial plane and transferred toward the aqueduct from the bilaminar structure in the DRN proper. Conversely, fibers are obviously more plentiful in the neuronal plane.

Another structure, extremely novel, and found in only two other parts of the brain has tentatively been identified in the subependyma. It is a vast syncytium of gap junction cells and fibers. A nervous syncytium is primarily a nineteenth century concept supposedly discredited by Ramon y Cajal using the Golgi Technique developed by Emilio Golgi. The syncytium consists of a network of both cells and fibers contiguous and providing for passage of chemicals from one cell to the next. Current art considers isolated connected cells, called gap junction cells, in a dynamic equilibrium with bounds forming and disappearing due to functional need. Only the electron microscope can definitively identify a gap junction connection.

The invention improves on the prior art by making visible either fibers that are normally devoid of serotonin or showing the rapid formation of a functional syncytia immediately following the synthesis of serotonin from L-tryptophan. Gap junctional complexes already known may, indeed, be extremely transitory structures.

"Two" putative gap junction cells in the medial subependyma at minutely separated focal planes less than one micron, the pattern of distribution of serotonin in any one location, varies considerably, suggesting that connections between cells and fibers are very frequent and complex in morphology forming a network.

Syncytia elsewhere, such as the thalamus, possess pacemaker activity. The syncytium in the medial subependyma is located near the lateral aqueductal tufts that project significantly into a vast ventricular system found throughout the central nervous system. The lateral tufts could play a major role in rhythmic propulsion of serotonin cephalad bathing the forebrain and synchronizing major neuronal functions. Disorders of desynchronization of neuronal activity could lead to numerous neuropathies not detectable by the prior art.

The syncytium herein described may have a characteristic not normally considered for syncytia, namely, a diffuse, localized accumulation of serotonin in a very circumscribed area between two or more cells, fibers, or cells and fibers. Normally, syncytia are conceptualized as being sharply delineated illustrated by a complex and subtle rearrangement of serotonergic stain within tiny to large fibers and cells and even within the extracellular matrix itself. The immunoserotonergic stain gives the impression that extracellular neurotransmitter may be a functional component of the subependymal syncytium.

The syncytium is in sharp focus at the top but not the bottom; the opposite sharpness occurs elsewhere in the syncytium. The objective used was a planapochromat. Had the objective been nonplan the outer circular one-third of the field would have been blurred. The only explanation for a rectangular area of sharpness sandwiched between dorsal and ventral blurred structures indicates a slanted subependymal plane, in this case with the face directed rostrad, supporting the contention of massive transport of serotonin cephalad.

Supraependymal cells have often been identified by the prior art, but never serotonergic supraependymal cells. Serotonergic supraependymal cells, cells at the interface of the ependyma and subependyma, and subependymal cells never described previously. They may be the same cells in different phases of a cyclic process. Diagnostically, they all contain numerous supraependymal-like varicose fibers, are stained intensely immunoserotonergic, and inhabit a similar location dorsal to the DRN proper in the lateral subependyma or ependyma. These cells exhibit some unique traits for normal physiology. The cell is intensely immunoserotonergic and uniformly stained. The various focal planes illustrate the numerous supraependymal fibers. A markedly granular cell with relatively few fibers and variable staining. This could be an involutional stage of the previous cell. The subependymal cells show a contiuum of cells jutting into the aqueduct are in the dorsal wall of the aqueduct and are continuous where the cell is at the interface of the ependyma and subependyma.

A still more bizarre cell is a very light-staining cell. In fact, they are numerous, once consciously sought.

The internal structure revealed by the serotonergic stain is not related to known cell morphology, however, the diagnostic characteristics described above are obvious, indicating that this is indeed a cell.

In 1977 it was hypothesized (Chan-Palay) that the sparing of supraependymal fibers in thiamine deficient rats (a model for Wernike-Korsakoff's syndrome) in the aqueductal region of the dorsal raphe may be related to a supraependymal cell not yet identified by the prior art. The cell above in FIG. 10 may be that cell in a quiescent state only visible transitorily during the burst of serotonergic synthesis initiated by the pretreatment with L-tryptophan herein applied 45 minutes prior to sacrifice.

This cell may exhibit a rapid cyclic nature from quiescence to intense serotonergic staining, from the dormant position in the subependyma to the transitional zone between the subependyma and ependyma where the supraependymal fibers proliferate to the supraependymal position. The serotonin in the supraependymal fibers may be secreted into the aqueduct as a neurohormone for distal distribution. 1625x.

In agreement with the above hypothesis the invention may reveal a vast network of varicose supraependymal fibers dorsal to and within the plane of the slanted rostral face of the subependyma. The previously described syncytium does not extend into the ependyma. The subtle variations in serotonergic immunoreactivity such as intensity, distribution, fiber size from gossamer to gross, and connectivity are not apparent. The diffuse immunoreactivity of the extracellular matrix is lacking. Immunoreactivity is found only in the fibers (there are no cells in this region). Individual fibers go in and out of focus without budding into new branches or revealing networks at immediately adjacent focal planes.

The slope is still evident.

The bilaminar structure may be related to a dopaminergic/serotonergic lamination in the cerebral cortex of the macaque (Berger et al) and special distributions of these two neurotransmitters in the macaque can be correlated with recent autopsied studies of cell loss in schizophrenia (Benes et al).

Schizophrenia is treated by neuroleptics, all of which are dopamine blockers. Dopamine is often a cotransmitter of serotonergic cells in the dorsal raphe.

Serotonin has been implicated in numerous psychiatric disorders: manic-depressive illness, other depressions, bulemia, anorexia nervose, disorders of the sleep-wakefulness cycle, sexuality and so on.

Conceivably, the etiologies of these disorders may occur occur in the brainstem. Specifically, schizophrenia has been thought of as a disease of the forebrain, but midbrain involvement has been discussed (Doty) and specific symptomotology may reside in the target tissue. The crossed fibers, in conjunction with uncrossed fibers arising in the dorsal raphe may ultimately terminate in the left or right cerebral hemispheres, producing the disorders recognized currently as schizophrenia and manic-depressive illness, respectively.

Numerous neurologic disorders involve serotonin including epilepsy.

The previous art neither stresses the considerable diversity of the DRN in the caudorostral and mediolateral directions nor does it point to specific locations where trace amines, implicated in the etiology of certain psychiatric diseases, have been found. Using a polarizing setup I have been able to locate plane polarized cells in very circumscribed areas of the glial plane of the bilaminar DRN.

Enzyme inhibitors of serotonergic metabolism, such as pargyline, used here (a monoamine oxidase inhibitor), or receptor blockers (both used clinically as antidepressants) in conjunction with L-tryptophan pretreatment may reveal changes different from L-tryptophan itself. The conversion of L-tryptophan may be especially related to insulin, a hormone believed now to be manufactured in the brain itself, and known to affect the passage of the amino acid precursor past the blood brain barrier to be converted to serotonin.

REFERENCES

Bauman et al. (1974) "Characteristics of tryptophan accumulation of glial cells." 66:253–263.

Benes et al. (1986) "Quantitative cytoarchitectural studies of the cerebral cortex of schizophrenics." Arch. Gen. Psychiatry, 43:31–35.

Berget et al. (1988) "Regional and laminar distribution of the dopamine and serotonin innervation in the macague cerebral cortex: a radioautographic study." J. Comp. Neurol., 273:99–119.

Chan-Palay, (1977) "Indoleamine neurons and their processes in the normal rat brain and in chronic diet-induced thiamine deficiency demonstrated by uptake of 3H-serotonin. J. Comp. Neurol. 176:467–494.

Descarries et al. (1982) "The serotonergic neurons in the nucleus dorsalis of the adult rat: A light and electron radioautographic study." J. Comp. Neurol. 207:239–254.

Doty, (1989) "Schizophrenia: a disease of interhemispheric processes at the forebrain and brainstem levels?" Behavioral Brain Res. 34:1–33.

Graham-Smith, (1971) "Studies in vivo on the relationship between brain tryptophan, brain 5-HT synthesis and hyperactivity in rats treated with a monoamine oxidase inhibitor and L-tryptophan." J. Neurochem. 18:1053–1066.

Hery et al. (1972) "Daily variations of serotonin metabolism in the rat brain." Brain Res. 43:445–465.

Pollack, Patent Number 4897380.

What is claimed is:

1. A method for examining a serotonergic tissue structure of a nonhuman vertebrate, comprising the steps of:
   (a) while the vertebrate is alive, intravenously administering L-tryptophan;
   (b) sacrificing the vertebrate at a time significantly less than one hour after completing said administration step and (c) thereafter examining a serotonergic tissue structure of said vertebrate using serotonin-sensitive examination means.

2. The method according to claim 1, wherein said vertebrate is sacrificed at a time more than five seconds but less than 55 minutes after completion of said administration step.

3. The method according to claim 1, wherein said vertebrate is sacrificed at a time on the order of 45 minutes after completion of said administration step.

4. The method according the claim 1, wherein the intravenous dose of L-tryptophan produces an effect distinct from no pretreatment.

5. The method according to claim 1, wherein the intravenous dose of L-tryptophan is 200 mg/kg.

6. The method according to claim 1, 2, or 3, comprising the additional step of injecting said vertebrate with a metabolic inhibitor of serotonin catabolism no more than 1.5 hours before said vertebrate is sacrificed.

7. The method according to claim 6, wherein said inhibitor is a monoamine oxidase.

8. The method according to claim 7, wherein said monoamine oxidase inhibitor is pargyline.

9. The method according to claim 6, wherein said vertebrate is a mammal.

10. The method according to claim 6, wherein said mammal is a rodent.

11. The method according to claim 6, wherein said mammal is a primate.

12. The method according to claim 1, comprising the additional step of subjecting said vertebrate to stress sufficient to produce a significant physiologic effect, and sacrificing said vertebrate before said physiological effect has abated.

13. The method according to claim 4 comprising the additional step of injecting said vertebrate with a serotonin-generation enhancing compound selected from the group consisting of insulin fructose, niacinamide, pyridoxine, calcium ascorbate, copper gluconate, and magnesium oxide while said vertebrate is alive.

14. The method according to claim 1, wherein said examining step comprises staining the tissue immunocytochemically for serotonin.

15. The method according to claim 1, wherein said examining step comprises visualizing microscopic monoamine-specific fluorescence of an immunofluorescent compound, comprising the steps of:
   (a) while the animal is alive, injecting an immunofluorescent compound;
   (b) treating the sectioned tissue by the indirect immunofluorescent technique with the tag fluorescein isothiocycanate (FITC); and
   (c) thereafter examining the serotonergic tissue structure in a microscope with a system revealing a blue excitation light of 455–490 nm with a red-free barrier set to selectively eliminate nonserotonergic tissue structures.

16. The method according to claim 15, wherein said immunofluorescent compound may be propidium iodide.

17. The method according to claim 1, wherein said examining step comprises labelling serotonergic tissue structures with a serotonin-tagged radioisotope.

18. The method according to claim 17 for examining a serotonergic structure comprising the step:
   (a) while the vertebrate is alive, intraventricular injection, freehand or by continuous pump infusion of a serotonin-tagged radioisotope.

19. The method according to claim 17, wherein serotonin-tagged radioisotope of a type containing tritium, [3H]serotonin.

20. The method according to claim 1, wherein said examining step comprises:
   (i) staining the tissue immunocytochemically for serotonin and, (ii) labelling serotonergic tissue structures with a serotonergic-tagged radioisotope.

21. The method according to claim 1, wherein said examining step comprises:

(i) staining the tissue immunofluorescently for serotonin and,
(ii) labelling serotonergic tissue structures with a serotonergic-tagged radioisotope.

* * * * *